United States Patent

Wetterich et al.

[11] Patent Number: 5,922,899
[45] Date of Patent: Jul. 13, 1999

[54] CARBAMOYL CARBOXYLIC ACID AMIDES

[75] Inventors: Frank Wetterich, Mutterstadt; Oliver Wagner, Bexbach; Karl Eicken, Wachenheim; Klaus Ditrich, Gönnheim; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 09/011,715

[22] PCT Filed: Aug. 26, 1996

[86] PCT No.: PCT/EP96/03755

§ 371 Date: Feb. 17, 1998

§ 102(e) Date: Feb. 17, 1998

[87] PCT Pub. No.: WO97/08138

PCT Pub. Date: Mar. 6, 1997

[30] Foreign Application Priority Data

Aug. 30, 1995 [DE] Germany .............. 195 31 814
Sep. 1, 1995 [DE] Germany .............. 195 32 313

[51] Int. Cl.$^6$ ................................. C07C 261/00
[52] U.S. Cl. .................................. 560/28
[58] Field of Search ............................ 560/28

[56] References Cited

FOREIGN PATENT DOCUMENTS

| | | |
|---|---|---|
| 2170059 | 3/1995 | Canada . |
| 43 21 897 | 1/1995 | Germany . |
| 95/08636 | 3/1995 | WIPO . |
| 96/07638 | 3/1996 | WIPO . |

OTHER PUBLICATIONS

Indian Journal of Chem. vol. 10, 1972, pp. 366–369.
Jrl. Am. Chem.Soc., vol. LVIII, Jul.–Dec., 1936, pp. 1808–1811.

*Primary Examiner*—Gary Geist
*Assistant Examiner*—Brian J. Davis
*Attorney, Agent, or Firm*—Keil & Weinkauf

[57] ABSTRACT

Carbamoylcarboxamides of the general formula I $$R^1-O-\underset{O}{\overset{\|}{C}}-NH-\underset{(S)}{\overset{H_3C\diagup CH \diagdown CH_3}{CH}}-\underset{O}{\overset{\|}{C}}-NH-\underset{(R)}{\overset{CH_3}{\overset{|}{CH}}}-\text{Naphthyl}-R^2 \quad (I)$$

($R^1$=unsubstituted or substituted alkyl, alkenyl, alkynyl; $R^2$=hydrogen, halogen, cyano, nitro, or unsubstituted or substituted alkyl, alkoxy, alkylthio, or an unsubstituted or substituted phenyl group which is bonded via oxygen or sulfur) and compositions comprising them, processes for their preparation, and the use of the compounds I and of the compositions.

7 Claims, No Drawings

CARBAMOYL CARBOXYLIC ACID AMIDES

The present invention relates to carbamoylcarboxamides of the general formula I

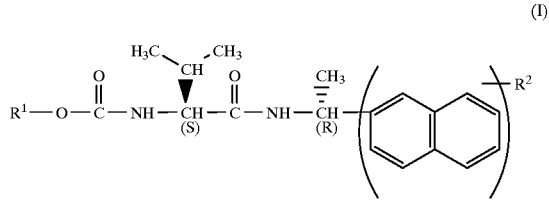

in an isomeric purity of more than 90% by weight where the variables have the following meanings:

$R^1$ is $C_1$–$C_8$alkyl, $C_2$–$C_8$-alkenyl or $C_2$–$C_8$-alkynyl,
  it being possible for these radicals to be partially or fully halogenated and/or to have attached to them one to three of the following groups: cyano, $C_1$–$C_4$-alkoxy, $C_1$–$C_4$-haloalkoxy, $C_1$–$C_4$-alkylthio, $C_1$–$C_4$-alkoxycarbonyl, $C_3$–$C_7$-cycloalkyl, $C_3$–$C_7$-cycloalkenyl, aryl, aryloxy and hetaryl,
  it being possible for the cyclic and aromatic rings of these groups, in turn, to have attached to them one to three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl;

$R^2$ is hydrogen, halogen, cyano, nitro, $C_1$–$C_8$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, or a phenyl group bonded via oxygen or sulfur which is unsubstituted or can have attached to it one to three of the following substituents: halogen, $C_1$–$C_4$-alkyl and $C_1$–$C_4$-alkoxy.

(S) represents the S configuration, (R) the R configuration of the asymmetric carbon atom thus marked, in accordance with the IUPAC nomenclature. In particular, the configuration of the S center in the compounds of the general formula I corresponds to the configuration of L-valine. For the sake of simplicity, the configuration of the compounds I will be termed (SR) configuration hereafter.

"Isomeric purity" refers to the percentage of a compound I (configuration (SR)) of the totality of the four diastereomers of these compounds I which are possible ((SR), (RS), (RR), (SS)).

Furthermore, the invention relates to processes for the preparation of the compounds I. The invention also relates to compositions which comprise the compounds I, to a process for the preparation of such compositions, and to a method of controlling harmful fungi and to the use of the compounds I or the compositions for this purpose.

Racemic mixtures of fungicidal compounds of the type I are disclosed mainly in DE-A 43 21 897 and in the earlier German Application P 44 31 467.1.

However, these mixtures are not yet satisfactory with a view to their fungicidal activity.

It is an object of the present invention to provide novel carbamoylcarboxamides with high isomeric purity which have an improved activity against harmful fungi.

We have found that this object is achieved by the compounds I defined at the outset and by compositions comprising them.

We have furthermore found processes for the preparation of the compounds I and of the compositions comprising them, and also a method of controlling harmful fungi and the use of the compounds I or the compositions for this purpose.

The compounds I can be prepared in a manner known per se starting from the corresponding carbamoylcarboxylic acids II which are based on L-valine. The compounds I are preferably obtainable by processes A and B described hereinbelow (the references "Houben-Weyl" refer to: Houben-Weyl, Methoden der Organischen Chemie [Methods in Organic Chemistry], 4th Edition, Thieme verlag, Stuttgart).

Process A

The carbamoylcarboxamides I are obtained by reacting the carbamoylcarboxylic acids II with the amines III.

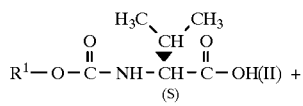

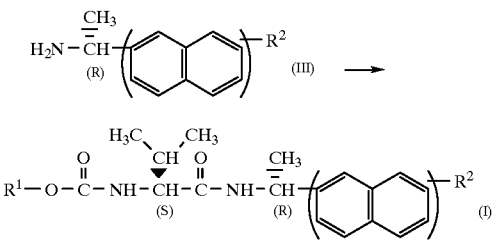

Those carbamoylcarboxylic acids II which are not already known can be prepared by known methods, especially starting from the amino acid L-valine (cf. "Houben-Weyl", Volume 15/1, page 46 to page 305, especially page 117 to page 125).

Equally, those amines III which are not already known can be obtained easily (cf. Organikum [Laboratory Practical Organic Chemistry], VEB Deutscher Verlag der Wissenschaften, 15th Edition, Berlin, 1977, page 610 et seq.; "Houben-Weyl", Volume 15/1, pages 648–665; Indian J. Chem. 10, page 366 (1972); J. Am. Chem. Soc. 58, pages 1808–1811 (1936)).

The R isomer can be separated from the racemates of the amines III in a manner known per se, for example by fractional crystallization with optically active tartaric acid or, preferably, by means of enzyme-catalyzed esterification followed by hydrolysis (cf., for example, WO-A 95/08636).

This process A is preferably carried out in such a manner that the carbamoylcarboxylic acids II are first converted into carboxyl-activated derivatives, especially acyl cyanides or anhydrides (cf. Tetrahedron Letters, Volume 18, page 1595 to page 1598 (1973), or "Houben-Weyl", Volume 15/1, page 28 to page 32). These derivatives are then reacted with the amines III in the presence of bases.

Suitable for the preparation of the carboxyl-activated acyl cyanides is, for example, the reaction of the carbamoylcarboxylic acids II with diethyl cyanophosphonate, especially in an inert solvent, such as tetrahydrofuran or toluene.

Preferred for the preparation of the carboxyl-activated anhydrides is the reaction of the carbamoylcarboxylic acid II with carbonic chlorides, such as isobutyl chloroformate, in the presence of bases and in the presence or absence of an inert solvent, such as toluene or tetrahydrofuran.

The reaction of the amines III with the carboxyl-activated carbamoylcarboxylic acids II is preferably carried out in a solvent such as dichloromethane, tetrahydrofuran or toluene.

Other substances which may act as bases are the amines III, and they are usually recovered usually [sic] from the crude product.

In a preferred embodiment of this process step, the carbamoylcarboxylic acid II, the amine III, the reagent which is suitable for producing the carboxyl-activated derivative of the carbamoylcarboxylic acid II and the base are reacted in a one-pot process in the presence or absence of an inert solvent, and the crude product is subsequently worked up in a manner known per se to give the carbamoylcarboxamide I.

Process B

The carbamoylcarboxamides I are obtained by converting the carbamoylcarboxamides I where the group $R^1$—O—(CO) is a protective group which can be eliminated in a manner known per se into amino acid amides IV and reacting the latter with chloroformic esters V in the presence of a of [sic] bases.

Stage Ba: Preparation of the amino acid amides IV

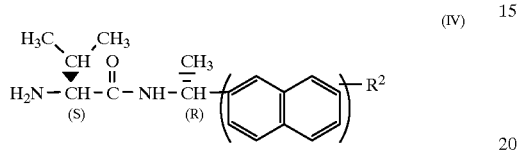

The elimination of the group $R^1$—O—(CO) from the carbamoylcarboxamides I can be carried out in a manner known per se (cf. "Houben-Weyl", Volume 15/1, page 46 to page 305, especially page 126 to page 129).

Suitable groups which can be eliminated contain, as radical $R^1$, the tert-butyl or and also the benzyl group.

In the event that $R^1$=tert-butyl, the elimination is usually carried out for example by means of reaction with an acid, in particular a protonic acid, such as hydrochloric acid or trifluoroacetic acid (ibid., page 126 to page 129).

The carbamoylcarboxamides I which are suitable as starting materials can be obtained by known processes (cf. "Houben-Weyl", Volume 15/1, page 28 to page 32) or, in particular, by process A according to the invention.

Step Bb: Preparation of the carbamoylcarboxamides I

The amino acid amides IV resulting from synthesis step (Ba) are reacted with the chloroformic esters V in the presence of bases.

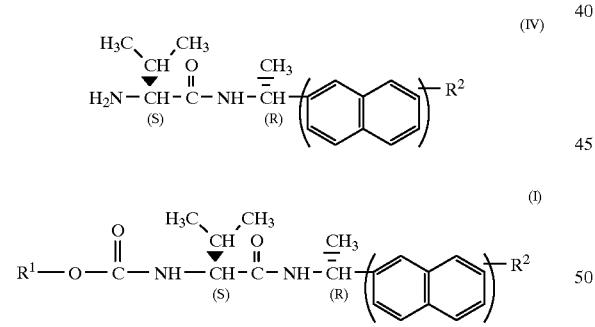

Those chloroformic esters V which are not generally known can be prepared by known processes.

The reaction is preferably carried out in an organic solvent, especially toluene, methylene chloride or tetrahydrofuran, or mixtures of these.

Both inorganic and organic bases are equally suitable, organic bases being preferred, and amongst these, in turn, tertiary amines, such as triethylamine, pyridine and N-methylpiperidine.

As a rule, the reaction is carried out at from (−40) to 50, preferably from (−10) to 20° C.

Besides, this reaction is known to those skilled in the art, and no further information is required in context with this (cf. "Houben-Weyl", Volume 15/1, page 117 to page 139).

The reaction mixtures obtained from processes A and B are worked up in the customary manner, eg. by mixing with water, phase separation and, if desired, chromatographic purification of the crude products. Some of the intermediates and end products are obtained in the form of colorless or pale brown viscous oils which can be freed from volatile components under reduced pressure and at moderately elevated temperatures. If the intermediates and end products are obtained in the form of solids, they may also be purified, for example by recrystallization or digestion.

The definition of the compounds I given at the outset used collective terms which represent the following substituents:

Halogen: fluorine, chlorine, bromine and iodine;

Alkyl: straight-chain or branched alkyl groups having 1 to 8 carbon atoms, eg. $C_1$–$C_6$-alkyl, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl, or partially or fully halogenated alkyl: straight-chain or branched alkyl groups having 1 to 4 or 8 carbon atoms (as indicated above), it being possible for the hydrogen atoms in these groups to be partially or fully replaced by halogen atoms (as indicated above), eg. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkoxy groups having 1 to 4 carbon atoms, eg. $C_1$–$C_3$-alkoxy, such as methyloxy, ethyloxy, propyloxy and 1-methylethyloxy;

Alkoxyalkyl: straight-chain or branched alkyl groups having 1 to 8 carbon atoms (as indicated above) which have, in any position, a straight-chain or branched alkoxy group (as indicated above) having, in the case of $C_1$–$C_4$-alkoxyalkyl, 1 to 4 carbon atoms, such as methoxymethyl, ethoxymethyl, n-propoxymethyl, n-butoxymethyl, 1-methoxyethyl, 2-methoxyethyl, 1-ethoxyethyl, 2-ethoxyethyl, 2-n-propoxyethyl and 2-butoxyethyl;

Haloalkoxy: straight-chain or branched alkoxy groups having 1 to 4 carbon atoms (as indicated above), it being possible for the hydrogen atoms in these groups to be partially or fully replaced by halogen atoms (as indicated above), eg. $C_1$–$C_2$-haloalkoxy, such as chloromethyloxy, dichloromethyloxy, trichloromethyloxy, fluoromethyloxy, difluoromethyloxy, trifluoromethyloxy, chlorfluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy;

Alkylthio: straight-chain or branched alkyl groups having 1 to 4 carbon atoms (as indicated above) which are bonded to the skeleton via a sulfur atom (—S—), eg. $C_1$–$C_4$-alkylthio, such as methylthio, ethylthio, propylthio, 1-methylethylthio, n-butylthio and tert-butylthio;

Alkoxycarbonyl: straight-chain or branched alkoxy groups having 1 to 4 C atoms (as indicated above) which are bonded to the skeleton via a carbonyl group (—CO—);

Alkenyl: straight-chain or branched alkenyl groups having 2 to 8 carbon atoms and a double bond in any position, eg. $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 2-methyl-1-propenyl, 1-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched alkynyl groups having 2 to 8 carbon atoms and a triple bond in any position, eg. $C_2$–$C_6$-alkynyl, such ethynyl, 1-propynyl, 2-propynyl, 1-butynyl, 2-butynyl, 3-butynyl, 1-methyl-2-propynyl, 1-penytynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Cycloalkyl: monocyclic alkyl groups having 3 to 7 carbon ring members, eg. $C_3$–$C_7$-cycloalkyl, such as cyclopropyl, cyclobutyl, cyclopentyl, cyclohexyl and cycloheptyl;

Cycloalkenyl: monocyclic alkyl groups having 5 to 7 carbon ring members which contain one or more double bonds, eg. $C_5$–$C_7$-cycloalkenyl, such as cyclopentenyl, cyclohexenyl and cycloheptenyl;

Aryloxy: aryl groups (as indicated above) which are bonded to the skeleton via an oxygen atom (—O—), such as phenoxy, 1-naphthoxy and 2-naphthoxy;

Hetaryl: aromatic mono- or polycyclic radicals which can additionally contain, besides carbon ring members, 1 to 4 nitrogen atoms or 1 to 3 nitrogen atoms -and one oxygen or one sulfur atom or one oxygen or one sulfur atom, eg.:

5-membered hetaryl containing 1 to 3 nitrogen atoms: 5-membered hetaryl ring groups which can contain, besides carbon atoms, 1 to 3 nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl, containing 1 to 4 nitrogen atoms or 1 to 3 nitrogen atoms and 1 sulfur atom or oxygen atom or 1 oxygen or 1 sulfur atom: 5-membered hetaryl ring groups which may contain, besides carbon atoms, 1 to 4 nitrogen atoms or 1 to 3 nitrogen atoms and 1 sulfur or oxygen atom or 1 oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl containing 1 to 3 nitrogen atoms or 1 nitrogen atom and/or one oxygen or sulfur atom: 5-membered hetaryl ring groups which can contain, besides carbon atoms, 1 to 4 nitrogen atoms or 1 to 3 nitrogen atoms and 1 sulfur or oxygen atom or 1 oxygen or one sulfur atom as ring members and in which 2 adjacent carbon ring members or 1 nitrogen and 1 adjacent carbon ring member can be bridged by a buta-1,3-diene-1,4-diyl group;

5-membered hetaryl, bonded via nitrogen and containing 1 to 4 nitrogen atoms, or benzo-fused 5-membered hetaryl, bonded via nitrogen and containing 1 to 3 nitrogen atoms: 5-membered hetaryl ring groups which may contain, besides carbon atoms, 1 to 4 nitrogen atoms, or 1 to 3 nitrogen atoms, as ring members and in which 2 adjacent carbon ring members, or one nitrogen and one adjacent carbon ring member can be bridged by a buta-1,3-diene-1,4-diyl group, these rings being bonded to the skeleton via one of the nitrogen ring members;

6-membered hetaryl containing 1 to 3, or 1 to 4, nitrogen atoms: 6-membered hetaryl ring groups which can contain, besides carbon atoms, 1 to 3, or 1 to 4, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl containing 1 to 4 nitrogen atoms: 6-membered hetaryl ring groups in which 2 adjacent carbon ring members may be bridged by a buta-1,3-diene-1,4-diyl group, eg. quinoline, isoquinoline, quinazoline and quinoxaline.

The term "partially or fully halogenated" is intended to express that in the groups thus characterized some or all of the hydrogen atoms can be replaced by identical or different halogen atoms, as indicated above.

Preferred compounds I with a view to their activity against harmful fungi are those which have an isomeric unit [sic] of not less than 93, in particular not less than 95%,.

Furthermore preferred compounds I with a view to their activity against harmful fungi are those where the radicals $R^1$ and $R^2$ have the following meanings, either alone or in combination. The groups mentioned hereinbelow in the meanings of radicals can also be substituted as indicated in the claims.

$R^1$ is $C_1$–$C_8$-alkyl, preferably $C_1$–$C_4$-alkyl, in particular isopropyl, tert-butyl or sec-butyl;

$R^2$ is hydrogen, halogen, cyano, $C_1$–$C_4$-alkyl or $C_1$–$C_4$-alkoxy, preferably hydrogen, chlorine, cyano, methyl or methoxy, in particular hydrogen.

Very particularly preferred with a view to their use are the compounds I compiled in Tables 1 and 2 below.

TABLE 1

| No. | $R^1$ | $R^2$ |
|---|---|---|
| 1.1 | $C(CH_3)_3$ | 4-Cl |
| 1.2 | $C(CH_3)_3$ | 5-Cl |
| 1.3 | $C(CH_3)_3$ | 6-Cl |
| 1.4 | $C(CH_3)_3$ | 7-Cl |
| 1.5 | $C(CH_3)_3$ | 8-Cl |
| 1.6 | $C(CH_3)_3$ | 4-$OCH_3$ |
| 1.7 | $C(CH_3)_3$ | 5-$OCH_3$ |
| 1.8 | $C(CH_3)_3$ | 6-$OCH_3$ |
| 1.9 | $C(CH_3)_3$ | 7-$OCH_3$ |
| 1.10 | $C(CH_3)_3$ | 8-$OCH_3$ |
| 1.11 | $C(CH_3)_3$ | 4-$CH_3$ |
| 1.12 | $C(CH_3)_3$ | 5-$CH_3$ |
| 1.13 | $C(CH_3)_3$ | 6-$CH_3$ |
| 1.14 | $C(CH_3)_3$ | 7-$CH_3$ |
| 1.15 | $C(CH_3)_3$ | 8-$CH_3$ |
| 1.16 | $CH(CH_3)_2$ | 4-Cl |
| 1.17 | $CH(CH_3)_2$ | 5-Cl |
| 1.18 | $CH(CH_3)_2$ | 6-Cl |
| 1.19 | $CH(CH_3)_2$ | 7-Cl |
| 1.20 | $CH(CH_3)_2$ | 8-Cl |
| 1.21 | $CH(CH_3)_2$ | 4-$OCH_3$ |
| 1.22 | $CH(CH_3)_2$ | 5-$OCH_3$ |
| 1.23 | $CH(CH_3)_2$ | 6-$OCH_3$ |
| 1.24 | $CH(CH_3)_2$ | 7-$OCH_3$ |
| 1.25 | $CH(CH_3)_2$ | 8-$OCH_3$ |
| 1.26 | $CH(CH_3)_2$ | 3-$CH_3$ |
| 1.27 | $CH(CH_3)_2$ | 4-$CH_3$ |
| 1.28 | $CH(CH_3)_2$ | 5-$CH_3$ |
| 1.29 | $CH(CH_3)_2$ | 6-$CH_3$ |
| 1.30 | $CH(CH_3)_2$ | 7-$CH_3$ |
| 1.31 | $CH(CH_3)_2$ | 8-$CH_3$ |
| 1.32 | $CH(CH_3)(C_2H_5)$ | 6-Cl |
| 1.33 | $CH(CH_3)(C_2H_5)$ | 7-Cl |
| 1.34 | $CH(CH_3)(C_2H_5)$ | 6-$OCH_3$ |
| 1.35 | $CH(CH_3)(C_2H_5)$ | 7-$OCH_3$ |
| 1.36 | $CH(CH_3)(C_2H_5)$ | 6-$CH_3$ |
| 1.37 | $CH(CH_3)(C_2H_5)$ | 7-$CH_3$ |
| 1.38 | $C(CH_3)_3$ | 6-CN |
| 1.39 | $CH(CH_3)_2$ | 6-CN |
| 1.40 | $CH(CH_3)(C_2H_5)$ | 6-CN |
| 1.41 | $C(CH_3)_3$ | 5-CN |
| 1.42 | $CH(CH_3)_2$ | 5-CN |
| 1.43 | $CH(CH_3)C_2H_5)$ | 5-CN |
| 1.44 | $C(CH_3)_3$ | 7-CN |
| 1.45 | $CH(CH_3)_2$ | 7-CN |
| 1.46 | $CH(CH_3)C_2H_5)$ | 7-CN |

Preferred compounds from amongst those mentioned in Table 1, in turn, are those in which the substituent $R^2$ is in the 5- or 6-position of the naphthalene ring system.

The novel compounds of the formula I are suitable for controlling harmful fungi.

For example, the novel compounds I can be applied in the form of directly sprayable solutions, powders, suspensions, also highly-concentrated aqueous, oily or other suspensions or dispersions, emulsions, oil dispersions, pastes, dusts, materials for spreading or granules by means of spraying, atomizing, dusting, scattering or pouring. The use forms depend on the intended purposes; in any case, they should guarantee the finest possible distribution of the active ingredients according to the invention.

For the treatment of plants, the plants will normally be sprayed or dusted with the active ingredients or the seeds of the plants will be treated with the active ingredients.

The formulations are prepared using customary formulation auxiliaries—as will be illustrated below—and in a manner known per se, eg. by extending the active ingredient with solvents and/or carriers, if desired using emulsifiers and dispersants, it being possible to use other organic solvents as auxiliary solvents if water is used as the diluent. Suitable auxiliaries are essentially: solvents, such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers, such as ground natural minerals (eg. kaolins, clays, talc, chalk) and ground synthetic minerals (eg. highly-disperse silica, silicates); emulsifiers, such as non-ionic and anionic emulsifiers (eg. polyoxyethylene fatty alcohol ethers, alkylsulfonates and arylsulfonates) and dispersants, such as ligninsulfite with liquors and methylcellulose.

Suitable surfactants are the alkali metal salt, alkaline earth metal salt and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates; and salts of sulfated hexa-, hepta- and octadecanols, and of fatty alcohol glycol ether; condensates of sulfonated naphthalene and its derivatives with formaldehyde, condensates of naphthalene or of the naphthalenesulfonic acids with phenol and formaldehyde, polyoxyethylene octylphenol [sic] ether, ethoxylated iso-octyl-, octyl- or nonylphenol, alkylphenol [sic] polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, eg. coated granules, impregnated granules and homogenous granules, can be prepared by binding the active ingredients to solid carriers. Solid carriers are mineral earths such as silica gel, silicas, silica gels [sic], silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders, or other solid carriers.

Examples of such preparations are:

I. a solution of 90 parts by weight of a compound I according to the invention and 10 parts by weight of N-methyl-2-pyrrolidone, which is suitable for use in the form of microdrops;

II. a mixture of 10 parts by weight of a compound I according to the invention, 70 parts by weight of xylene, 10 parts by weight of the adduct of 8 to 10 mole of ethylene oxide to 1 mole of oleic acid N-monoethanolamide, 5 parts by weight of calcium dodecylbenzene sulfonate, 5 parts by weight of the adduct of 40 mole of ethylene oxide to 1 mole of castor oil; a dispersion is obtained by finely distributing the solution in water.

III. an aqueous dispersion of 10 parts by weight of a compound I according to the invention, 40 parts by weight of cyclohexanone, 30 parts by weight of isobutanol, 20 parts by weight of the adduct of 40 mole of ethylene oxide to 1 mole of castor oil;

IV. an aqueous dispersion of 10 parts by weight of a compound I according to the invention, 25 parts by weight of cyclohexanol, 55 parts by weight of a mineral oil fraction of boiling point 210 to 280° C. and 10 parts by weight of the adduct of 40 mole of ethylene oxide to 1 mole of castor oil;

V. a mixture, ground in a hammer mill, of 80 parts by weight of preferably a solid compound I according to the invention, 3 parts by weight of sodium diisobutylnaphthalene-2-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 62 parts by weight of pulverulent silica gel and 8 parts by weight of paraffin oil which had been sprayed onto the surface of this silica gel; this formulation imparts good adhesion properties to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 50 parts by weight of a paraffinic mineral oil.

The novel compounds are distinguished by an outstanding activity against a broad spectrum of phytopathogenic fungi, in particular from the class of the Phycomycetes and also from the classes of the Deuteromycetes, Ascomycetes and Basidiomycetes. Some of them act systemically and can be employed as leaf- and foliar-acting fungicides.

They are especially important for controlling a large number of fungi which infect a variety of crop plants such as wheat, rye, barley, oats, rice, maize, lawns, cotton, soya beans, coffee, sugar cane, grapevines, fruit species, ornamentals and vegetable species such as cucumbers, beans and cucurbits, and the seeds of these plants.

The compounds are applied by treating the harmful fungi, their environment, or the plants, spaces, areas or materials to be kept free from them, with an effective amount of the active ingredients.

Application is effected before or after infection of the materials, plants or seeds by the fungi.

Specifically, the novel compounds are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, grapevines, ornamentals and vegetables, *Cercospora arachidicola* on groundnuts, *Pseudocercosporella herpotrichoides* on wheat and barley, *Pyricularia oryzae* on rice, *Phytophthora infestans* on potatoes and tomatoes, *Pseudoperenospora cubensis* on cucumbers, Fusarium and Verticillium species on variety of plants, *Plasmopara viticola* on grapevines, *Pseudoperenospora humuli* on hops and Alternaria species on vegetables and fruit.

The novel compounds can also be employed in the protection of materials (protection of wood), eg. against *Paecilomyces variotii*.

In general, the fungicidal compositions comprise from 0.1 to 95, preferably from 0.5 to 90%, by weight of active ingredient.

Depending on the nature of the desired effect, the rates of application are from 0.025 and 2, preferably 0.1 to 1 kg of active ingredient per ha.

For the treatment of seeds, amounts of active ingredient of from 0.001 to 50, preferably 0.01 to 10 g, are generally required per kilogram of seed.

In the use form as fungicides, the compositions according to the invention may also be present together with other active ingredients, eg. with herbicides, insecticides, growth regulators, fungicides or else fertilizers.

Mixtures with fungicides frequently result in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl) disulfide;

nitro derivatives, such as dinitro(1-methylheptyl) phenylcrotonate, 2-sec-butyl-4,6-dinitrophenyl 3,3-dimethylacrylate, 2-secbutyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimid-azolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thiol 1-oxide, 8-hydroxyquinoline or its copper salt, 2,3-dihydro-5-carboxanilido-6-methyl-1,4-oxathine, 2,3-dihydro-5-carboxanilido-6-methyl-1,4-oxathine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl)-formamide [sic], 1-(3,4-dichloroanilino)-1-formylamino-2,2,2-trichloroethane, 2,6-dimethyl-N-tridecyl-morpholine or its salts, 2,6-dimethyl-N-cyclododecylmorpholine or its salts, N-[3-(p-tert-butylphenyl)-2-methylpropyl]-cis-2,6-dimethylmorpholine, N-[34-(p-tertbutylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxy-ethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, 1-[3-(2-chlorophenyl)-1-(4-fluorophenyl)oxiran-2-yl-methyl]-1H-1,2,4-triazole, and a variety of fungicides such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)DL-alaninate, DL-N-(2,6-dimethyl-phenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[(3,5-dichlorophenyl)-5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole, strobilurins such as methyl E-methoximino-[α-(o-tolyloxy)-o-tolyl]acetate, methyl E-2-{2-[6-(2-cyanophenoxy) pyridimin-4-yloxy]phenyl}-3-methoxyacrylate, methyl E-methoximino-[α-(2,5-dimethyloxy)-o-tolyl]acetamide.

aminopyridine such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline.

phenylpyrrols such as 4-(2,2-difluoro-1,3-benzodioxol-4-yl)pyrrole-3-carbonitrile.

cinnamides such as 3-(4-chlorophenyl)-3-(3,4-dimethoxyphenyl)acryloylmorpholine.

Synthesis Example

The protocol shown in the synthesis example below can be used for obtaining other representatives of the compounds I by modifying the starting compound. The physical data of the products prepared following this protocol are shown in Table 2 which follows.

1. (R)-1-Amino-1-(β-naphthyl)ethane 1.1 Preparation of (R)-N-[1-(β-naphthyl)ethyl]methoxyacetamide

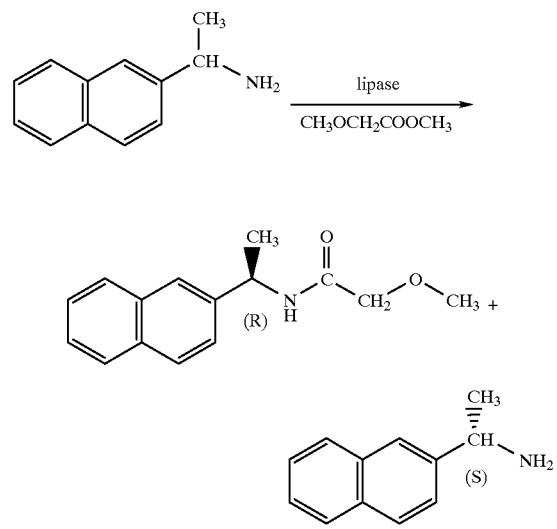

39 g (0.23 mol) of racemic 1-amino-1-(β-naphthyl)ethane were dissolved in 200 ml of methyl tert-butyl ether. The solution was treated with 29.5 g (0.25 mol) of methyl methoxyacetate, the reaction was started by adding 0.5 g of lipase (approximately 1,000 U/mg, Pseudomonas spec. DSM 8246), and the batch was mixed during the reaction on a vibrating table. After the reaction rate had reached 50% (check by means of gas chromatography), which was the case after approximately 48 hours, the enzyme was filtered off. The filtrate was concentrated and the concentrate taken up in dilute hydrochloric acid (300 ml) and diethyl ether (300 ml). After the ether phase had been separated off, the acid phase was re-extracted using diethyl ether. After the ether phases had been combined, dried and concentrated, 18.7 g (0.08 mol) of (R)-N-[1-(β-naphthyl)ethyl]methoxyacetamide were obtained. After addition of sodium hydroxide solution until the pH is alkaline, it was possible to extract (S)-1-amino-1-(β-naphthyl)ethane from the aqueous phase with diethyl ether. Drying and evaporation of the organic phase gave 15 g of (0.09 mol) of (S)-1-amino-1-(β-naphthyl)ethane. After reaction to give the trifluoroacetamide, the enantiomeric excess (=ee) was determined on a chiral GC column (20 m Chiralolex B-Ph) as 89.5%.

1.2 Hydrolysis of (R)-N-[1-(β-naphthyl)ethyl] methoxyacetamide

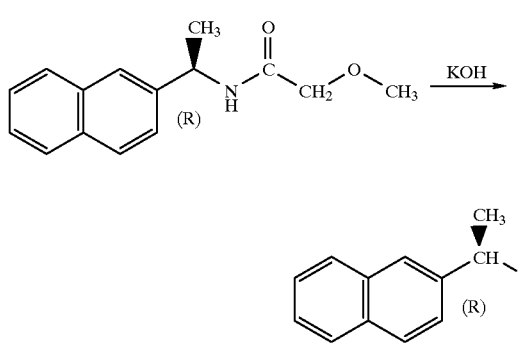

14.7 g (60.4 mmol) of (R)-N-[1-(β-naphthyl)ethyl] methoxyacetamide were dissolved in 75 ml of ethylene glycol, and 15 g of 50% strength potassium hydroxide solution were added. After the mixture had been heated for 3 hours at 150° C., it was cooled, diluted with 300 ml of water and extracted four times using in each case 500 ml of diethyl ether. The combined ether phases were dried and concentrated. This gave 8.1 g (47 mmol) of (R)-1-amino-1-(β-naphthyl)ethane with an ee value of 94.8%.

2. N-(tert-Butyloxycarbonyl)-L-valine (R)-1-naphthylethylamide 1.0 g (5.9 mmol) of diethyl cyanophosphate and 1.3 g (12 mmol) of triethylamine were added to a solution of 1.2 g (5.8 mmol) of tert-butoxycarbonyl-L-valine and 1.0 g (5.8 mmol) of (R)-1-amino-1-(β-naphthyl)ethane in 50 ml of tetrahydrofuran. Stirring was continued for one hour at 0° C./ and for 15 hours at 20° C. The solvent was subsequently removed and the residue was taken up in 300 ml of ethyl acetate. The organic phase was washed in succession with in each case 200 ml of 5% strength sodium hydroxide solution, 10% strength hydrochloric acid, 10% strength sodium hydrogen carbonate solution and water, dried and concentrated. 2.0 g (5.4 mmol) of N-(tert-butyloxycarbonyl)-L-valine (R)-1-β-naphthylethylamide remained (m.p. 93° C., Compound 2.1 in Table 2).

3. N-(Isopropyloxycarbonyl)-L-valine (R)-1-(β-naphthyl) ethylamide 5 ml of trifluoroacetic acid were added to 1.70 g (4.6 mmol) of N-(tert-butyloxycarbonyl)-L-valine (R)-1-(β-naphthyl)ethylamide, with cooling, and the mixture was stirred for 1 hour at 0° C. It was subsequently heated at 20° C., most of the trifluoroacetic acid was distilled off, and the residue was taken up in 100 ml of dichloromethane and washed in succession with in each case 50 ml of 2N sodium hydroxide solution, 5% strength sodium hydrogen carbonate solution and water. After the organic phase had been dried and concentrated, 1.07 g (4.0 mmol) of L-valine (R)-1-(β-naphthyl)ethylamide remained as a yellow viscous oil.

0.54 g (2.0 mmol) of this compound and 0.22 g (2.2 mmol) of triethylamine in 40 ml of toluene were treated with 0.24 g (2.1 mmol) of isopropyl chloroformate at 0° C. and the mixture was stirred for 15 hours at 20° C. After the solvent had been removed, the residue was taken up in 50 ml of ethyl acetate and washed in succession using in each case 40 ml of 5% strength sodium hydroxide solution, 10% strength hydrochloric acid, 10% strength sodium hydrogen carbonate solution and water. After the organic phase had been dried, the solvent was removed. 0.6 g (1.7 mmol) of the title compound remained as a colorless crystalline residue (m.p. 145–7° C., Compound 2.2 in Table 2).

TABLE 2

(I)

R$^1$—O—C(=O)—NH—CH(CH(CH$_3$)$_2$)—C(=O)—NH—CH(CH$_3$)—(β-naphthyl)—R$^2$
(S)                                      (R)

| No. | R$^1$ | R$^2$ | M.p. [° C.] |
|-----|-------|-------|-------------|
| 2.1 | C(CH$_3$)$_3$ | H | 90–3 |
| 2.2 | CH(CH$_3$)$_2$ | H | 145–7 |

Use Examples

In the experiments below, which are intended to demonstrate the fungicidal activity of the compounds I, an emulsion was used which was composed of 10% by weight of the active ingredient of the general formula I and of 90% by weight of a mixture of 70% by weight of cyclohexanol, 20% by weight of Nekanil® LN (Lutensol® AP6, wetting agent having emulsifying and dispersant action based on ethoxylated alkylphenols) and 10% by weight of Emulphor® EL (Emulan®EL, emulsifier based on ethoxylated fatty alcohols).

desired concentration of active ingredient was adjusted by diluting this emulsion with water.

*Plasmopara viticola*

Leaves of grapevines cv. "Müller-Thurgau" in pots were sprayed with an aqueous spray mixture which had been prepared as described above. To be able to assess the duration of action of the active ingredient, the plants were placed in the greenhouse for 8 days after the spray coating had dried. Only then were the leaves infected with a zoospore suspension of *Plasmopara viticola* (downy mildew of grapevine). The vines were first placed into a chamber with water-vapor-saturated air at 24° C. for 48 hours and then in a greenhouse at from 20 to 30° C. for 5 days. After this time, the plants were returned into the humid chamber for 16 hours to promote the eruption of sporangiophores. The extent of fungal eruption on the underside of the leaves was then assessed visually. The test results can be seen in Table 3 below.

TABLE 3

Test results with compounds according to the invention in comparison with the racemates comprising them (disclosed in DE-A 43 21 897) in *Plasmopara viticola*

| Active ingredient | Diseased leaf-underside area (%) at a concentration of active ingredient applied of: | | | |
|---|---|---|---|---|
| | 63 ppm | 16 ppm | 4 ppm | 1 ppm |
| 2.1 | 0 | 3 | 5 | 15 |
| Racemate pertaining to 2.1 | 0 | 15 | 40 | — |

TABLE 3-continued

Test results with compounds according to the invention in comparison with the racemates comprising them (disclosed in DE-A 43 21 897) in *Plasmopara viticola*

| Active ingredient | Diseased leaf-underside area (%) at a concentration of active ingredient applied of: | | | |
|---|---|---|---|---|
| | 63 ppm | 16 ppm | 4 ppm | 1 ppm |
| 2.2 | 0 | 0 | 0 | 0 |
| Racemate pertaining to 2.2 | 0 | 3 | 25 | 40 |

The leaves of plants which had not been treated with one of the abovementioned compounds showed fungal disease on 75% of the leaf-underside area.

We claim:

1. A carbamoylcarboxamide of the general formula I

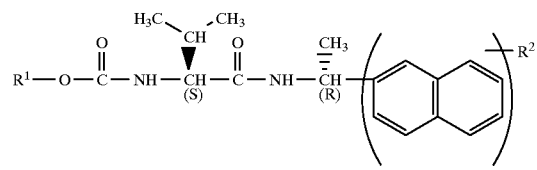

(I)

in an isomeric purity of more than 90% by weight where the variables have the following meanings:

$R^1$ is $C_1$–$C_8$-alkyl, $C_2$–$C_8$-alkenyl or $C_2$–$C_8$-alkynyl,
it being possible for these radicals to be partially or fully halogenated and/or to have attached to them one to three of the following groups: cyano, $C_1$–$C_4$-alkoxy, $C_1$–$C_4$-haloalkoxy, $C_1$–$C_4$-alkylthio, $C_1$–$C_4$-alkoxycarbonyl, $C_3$–$C_7$-cycloalkyl, $C_3$–$C_7$-cycloalkenyl, aryl, aryloxy and hetaryl,
it being possible for the cyclic and aromatic rings of these groups, in turn, to have attached to them one to three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl;

$R^2$ is hydrogen, halogen, cyano, nitro, $C_1$–$C_8$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio or or a phenyl group bonded via oxygen or sulfur which is unsubstituted or can have attached to it one to three of the following substituents: halogen, $C_1$–$C_4$-alkyl and $C_1$–$C_4$-alkoxy.

2. A process for the preparation of a carbamoylcarboxamide of the general formula I as claimed in claim 1, which comprises reacting a carbamoylcarboxylic acid of the general formula II

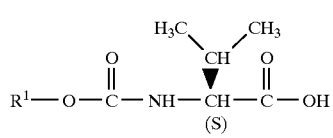

(II)

with an amine of the general formula III.

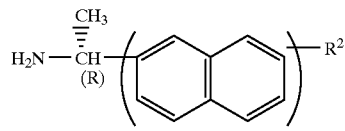

(III)

3. A process for the preparation of a carbamoyl carboxamide of the general formula I as claimed in claim 1, which comprises a) converting a carbamoylcarboxamide of the general formula I

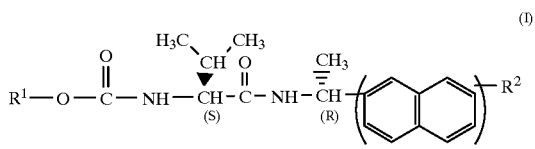

(I)

where the group $R^1$—O—(CO) is a protective group which can be eliminated in a manner known per se into an amino acid amide IV

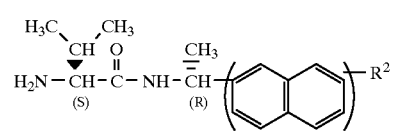

(IV)

and b) reacting the resulting amino acid amide IV with a chloroformic ester of the general formula V

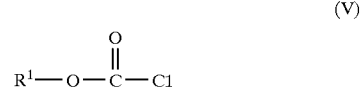

(V)

in the presence of a base.

4. A composition for controlling harmful fungi, comprising an effective amount of at least one compound of the formula I as defined in claim 1 and at least one customary formulation auxiliary.

5. A process for the preparation of a composition as defined in claim 4, which process comprises combining a fungicidally active amount of at least one compound of the formula I as defined in claim 1 together with at least one customary formulation auxiliary.

6. A method of controlling harmful fungi, which method comprises treating the harmful fungi, their environment, or the plants, spaces, areas or materials to be kept free from the fungi, with an effective amount of at least one compound of the formula I as defined in claim 1.

7. A method of controlling harmful fungi, which method comprises treating the harmful fungi, their environment, or the plants, spaces, areas or materials to be kept free from the fungi, with an effective amount of the composition defined in claim 4.

* * * * *